US008084252B2

(12) United States Patent
Reiter et al.

(10) Patent No.: US 8,084,252 B2
(45) Date of Patent: *Dec. 27, 2011

(54) RECOMBINANT CELL CLONES HAVING INCREASED STABILITY AND METHODS OF MAKING AND USING THE SAME

(75) Inventors: Manfred Reiter, Vienna (AT); Wolfgang Mundt, Vienna (AT); Friedrich Dorner, Vienna (AT)

(73) Assignee: Baxter Innovations GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 12/848,897

(22) Filed: Aug. 2, 2010

(65) Prior Publication Data

US 2010/0317055 A1 Dec. 16, 2010

Related U.S. Application Data

(60) Division of application No. 12/488,465, filed on Jun. 19, 2009, which is a continuation of application No. 11/482,504, filed on Jul. 7, 2006, now abandoned, which is a division of application No. 11/123,362, filed on May 6, 2005, now Pat. No. 7,094,575, which is a continuation of application No. 10/170,661, filed on Jun. 12, 2002, now Pat. No. 6,936,441, which is a continuation of application No. 09/324,612, filed on Jun. 2, 1999, now Pat. No. 6,475,725, which is a continuation-in-part of application No. 09/100,253, filed on Jun. 19, 1998, now Pat. No. 6,100,061.

(30) Foreign Application Priority Data

Jun. 20, 1997 (AT) ........................ 1073/97

(51) Int. Cl.
*C12N 15/85* (2006.01)
*C12N 15/09* (2006.01)
*C12P 21/00* (2006.01)
(52) U.S. Cl. .................... 435/325; 435/455; 435/70.1
(58) Field of Classification Search .................. None
See application file for complete search history.

(56) References Cited

U.S. PATENT DOCUMENTS

| 4,431,629 A | 2/1984 | Olsen |
| 4,443,540 A | 4/1984 | Chervan et al. |
| 4,767,704 A | 8/1988 | Cleveland et al. |
| 4,978,616 A | 12/1990 | Dean, Jr. et al. |
| 5,122,469 A | 6/1992 | Mather et al. |
| 5,316,938 A | 5/1994 | Keen et al. |
| 5,378,612 A | 1/1995 | Nakashima et al. |
| 5,393,668 A | 2/1995 | Cinatl et al. |
| 5,441,868 A | 8/1995 | Lin |
| 5,573,937 A | 11/1996 | Shinmoto et al. |
| 5,633,162 A | 5/1997 | Keen et al. |
| 5,719,050 A | 2/1998 | Hashimoto et al. |
| 5,741,705 A | 4/1998 | Blom et al. |
| 5,789,247 A | 8/1998 | Ballay et al. |
| 5,804,420 A | 9/1998 | Chan et al. |
| 5,811,299 A | 9/1998 | Renner et al. |
| 5,851,800 A | 12/1998 | Adamson et al. |
| 5,885,835 A | 3/1999 | Blom et al. |
| 6,048,728 A | 4/2000 | Inlow et al. |
| 6,100,061 A | 8/2000 | Reiter et al. |
| 6,114,146 A | 9/2000 | Herlitschka et al. |
| 6,475,725 B1 | 11/2002 | Reiter |
| 2002/0182679 A1 | 12/2002 | Reiter et al. |
| 2003/0203448 A1 | 10/2003 | Reiter et al. |
| 2006/0148074 A1 | 7/2006 | Gorfien et al. |

FOREIGN PATENT DOCUMENTS

| AT | 1659/99 A | 9/1999 |
| AU | 78958/98 A | 10/1998 |
| AU | 199953636 | 3/2001 |
| CA | 2161517 A1 | 11/1994 |
| EP | 0 160 457 B1 | 11/1985 |
| EP | 0 481 791 A2 | 4/1992 |
| EP | 0 485 689 A1 | 5/1992 |
| EP | 0 631 731 A1 | 1/1995 |
| EP | 0 666 312 A1 | 8/1995 |
| EP | 0 711 835 A1 | 5/1996 |
| EP | 0 872 487 A2 | 10/1998 |
| EP | 00 120 896.6 | 9/2000 |
| EP | 1 200 561 B1 | 6/2006 |
| FR | 2 196 386 A | 3/1974 |
| JP | 3-244391 | 10/1991 |
| JP | 4-316484 | 11/1992 |
| JP | 5-123178 A | 5/1993 |
| JP | 7-039386 A | 2/1995 |
| JP | 2-859679 B2 | 2/1999 |
| JP | H01-211488 A | 8/1999 |
| WO | WO 85/02610 A1 | 6/1985 |

(Continued)

OTHER PUBLICATIONS

Berg, D.T. et al.; "High-Level Expression of Secreted Proteins from Cells Adapted to Serum-Free Suspension Culture"; *BioTechniques*; 1993 vol. 14(6); pp. 972-978.

Bielicki, J. et al.; "Recombinant Human Sulphamidase: Expression, Amplification, Purification and Characterization"; 1998; *Biochem. J.*; vol. 329; pp. 145-150.

Brown, M.E. et al.; "Process Development for the Production of Recombinant Antibodies Using the Glutamine Synthetase (GS) System"; 1992; *Cytotechnology*; vol. 9; pp. 231-236.

Burger, C. et al.; "An Integrated Strategy for the Process Development of a Recombinant Antibody-Cytokine Fusion Protein Expressed in BHK Cells"; 1999; *Appl. Microbiol. Biotechnol.*; vol. 52; pp. 345-353.

(Continued)

*Primary Examiner* — Michele K Joike (74) *Attorney, Agent, or Firm* — Kilpatrick Townsend & Stockton LLP (57) ABSTRACT

Disclosed are a stable recombinant cell clones which are stable in serum- and protein-free medium for at least 40 generations, a biomass obtained by multiplying the stable cell clone under serum- and protein-free culturing conditions, and a method of preparing recombinant proteins by means of the biomass. Furthermore, the invention relates to a method of recovering stable recombinant cell clones.

21 Claims, 3 Drawing Sheets

FOREIGN PATENT DOCUMENTS

| | | |
|---|---|---|
| WO | WO 86/04920 A1 | 8/1986 |
| WO | WO 88/00967 A1 | 2/1988 |
| WO | WO 89/00192 A1 | 1/1989 |
| WO | WO 91/09122 A1 | 6/1991 |
| WO | WO 91/10726 A1 | 7/1991 |
| WO | WO 94/25599 A1 | 11/1994 |
| WO | WO 96/07730 A2 | 3/1996 |
| WO | WO 96/07730 A3 | 3/1996 |
| WO | WO 96/15231 A1 | 5/1996 |
| WO | WO 96/18734 A1 | 6/1996 |
| WO | WO 96/26266 A1 | 8/1996 |
| WO | WO 96/40866 A1 | 12/1996 |
| WO | WO 97/05240 A1 | 2/1997 |
| WO | WO 98/08934 A1 | 3/1998 |
| WO | WO 98/15614 A1 | 4/1998 |
| WO | WO 98/54296 A1 | 12/1998 |
| WO | WO 99/05268 A1 | 2/1999 |
| WO | WO 99/57246 A1 | 11/1999 |
| WO | WO 00/03000 A2 | 1/2000 |
| WO | WO 01/11021 A1 | 2/2001 |
| WO | WO 01/14529 A1 | 3/2001 |
| WO | WO 01/23527 A1 | 4/2001 |
| WO | WO 02/24876 A2 | 3/2002 |
| WO | WO 02/24876 A3 | 3/2002 |
| WO | WO 2004/005493 A1 | 1/2004 |

OTHER PUBLICATIONS

Cartier, M. and Stanners, C.P.; "Stable, High-Level Expression of a Carcinoembryonic Antigen-encoding cDNA After Transfection and Aplification with the Dominant and Selectable Asparagine Synthetase Marker" ; 1990; *Gene*; vol. 95; pp. 223-230.

Cole, E.S. et al.; "Recombinant Human Thyroid Stimulating Hormone: Development of a Biotechnology Product for Detection of Metastatic Lesions of Thyroid Carcinoma"; Sep. 1993; *Biotechnology*; vol. 11; pp. 1014-1024.

Cruz, H.J. et al.; "Adaptation of BHK Cells Producing a Recombinant Protein to Serum-Free Media and Protein-Free Medium"; 1998; *Cytotechnology*; vol. 26; pp. 59-64.

Donaldson, M.S. and Sculer, M.L.; "Low-Cost Serum-Free Medium for the BTI-Tn5B1-4 Insect Cell Line"; 1998; *Biotechnol. Prog.*; vol. 14; pp. 573-579.

Doyle, A. et al. eds.; "Cloning"; Part 4D Module 4D1 *In Cell & Tissue Cultrue: Laboratory Porcedures*; 1998; John Wiley & Sons; London Cloning Techniques (Non-hybridoma Related); pp. 4D:1.1-4D:1.9.

Eagle, H.; "Amino Acid Metabolism in Mammalian Cell Cultures"; Aug. 21, 1939; *Science*; vol. 130; pp. 432-437.

Farrell, P.J. et al.; "High-Level Expression of Secreted Glycoproteins in Transformed Lepidopteran Insect Cells Using a Novel Expression Vector"; Dec. 20, 1998; *Biotechnology and Bioengineering*; vol. 60(6); pp. 656-663.

Faure, T. et al.; "Stable Expression of Coagulation Factors FVIII and Fix in Recombinant Chinese Hamster Ovary Cells"; 1989; Meeting Info. 9$^{th}$ General Meeting of the European Society for Animal Cell Technology; Knokke (Belgium); 1988; pp. 481-488.

Field, R.P. et al.; "Production of a Chimeric Antibody for Tumour Imaging and Therapy From Chinese Hamster Ovary (CHO) and Myeloma Cells"; May 1990; *Proceedings of the 10$^{th}$ ESACT Meeting*; pp. 742-744.

Fischer, B. et al.; "Comparison of N-Glycan Pattern of Recombinant Human Coagulation Factors II and IX Expressed in Chinese Hamster Ovary (CHO) and African Green Monkey (Vero) Cells"; 1996; *J. Thrombos. and Trombolys.*; vol. 3; pp. 57-62.

Fischer, B.E. et al.; "Biochemical and Functional Characterization of Recombinant von Willebrand Factor Produced on a Large Scale"; 1997; *CMLS*; vol. 53; pp. 943-950.

Fischer, B.E. et al.; "Structural Analysis of Recombinant von Willebrand Factor Produced at Industrial Scale Fermentation of Transformed CHO Cells Co-expressing Recombinant Furin"; 1995; *FEBS Letters*; vol. 375; pp. 259-262.

Fischer et al.; "Structural Analysis of Recombinant von Willebrand Factor: Identification of Hetero- and Homo-Dimers"; 1994; *FEBS Letters*; vol. 351; pp. 345-348.

Franek, F. et al; "Plant Protein Hydrolysates: Preparation of Defined Peptide Fractions Promoting Growth and Production in Animal Cells Cultures"; 2000; *Biotechnol. Prog.*; vol. 16(5); pp. 688-692.

Freshney, R.I.; "The Culture Environment: Substrate, Gas Phase, Medium, and Temperature"; Chapter 7 *In Culture of Animal Cells a Manual of Basic Technique*, 2$^{nd}$ Edition; 1987; pp. 57-84.

Friedman, J.S. et al.; "High Expression in Mammalian Cells Without Amplification"; Apr. 1989; *Biotechnology*; vol. 7; pp. 359-362.

Gandor, C.; "Amplification and Expression of Recombinant Genes in Serum-Independent Chinese Hamster Ovary Cells"; 1995; *FEBS Letters*; vol. 377; pp. 290-294.

Gorfien, S.F. et al.; "Recombinant Protein Production by CHO Cells Cultured in a Chemically Defined Medium"; 1996; presented at JAACT, Yokohama: Japan; 16 pages.

Haldankar, R, et al.; "Stable Production of a Human Growth Hormone Antagonist From CHO Cells Adapted to Serum-Free Suspension Culture"; 1999; *Biotechnol. Prog.*; vol. 15(3); pp. 336-346.

Ham, R.G.; "Clonal Growth of Mammalian Cells in a Chemically Defined, Synthetic Medium"; 1965; *PNAS*; vol. 53; pp. 288-293.

Harant, H. et al.; "Two-Dimensional Electrophoresis as a Tool For Control of Quality and Consistency in Production Systems Using Animal Cells"; 1992; *Cytotechnology*; vol. 8; pp. 119-127.

Harrison, S. et al.; "The Manufacturing Process for Recombinant Factor IX"; Apr. 1998; *Seminars in Hematology*; vol. 35(2), Suppl. 2; pp. 4-10.

Hassell, T. et al.; "Stability of Production of Recombinant Antibodies from Glutamine Synthetase Amplified CHO and NS0 Cell Lines"; 1992; *Animal Cell Technology: Developments, Processes and Products*, 11$^{th}$ ESACT Meeting; pp. 42-47.

Heidemann, R. et al.; "The Use of Peptones as Medium Additives for High-Density Perfusion Cultures of Animal Cells"; Poster Presented at the 16th ESACT Meeting, Apr. 25-29, 1999, Lugano, Switzerland; 3 pages.

Heidermann, R. et al.; "The Use of Peptones as Medium Additives for the Production of a Recombinant Therapeutic Protein in High Density Perfusion Cultures of Mammalian Cells"; 2000; *Cytotechnology*; vol. 32; pp. 157-167.

Hsieh, C.M. et al.; "The Effect of Soy Protein Hydrolyzates on Fermentation by *Lactobacillus amylovorus*"; 1999; *Process Biochemistry*; vol. 34; pp. 173-179.

Inoue, Y. et al.; "Production of Recombinant Human Monoclonal Antibody Using *ras*-Amplified BHK-21 Cells in a Protein-free Medium"; 1996; *Biosci. Biotech. Biochem.*; vol. 60(5); pp. 811-817.

Ito, Y. et al.; "Protein-Free Cell Culture on an Artificial Substrate with Covalently Immobilized Insulin"; 1996; *Proc. Natl. Acad. Sci. USA*; vol. 93; pp. 3598-3601.

Jan, D.C-H. et al.; "Peptone, a Low-Cost Growth-Promoting Nutrient for Intensive Animal Cell Culture"; *Cytotechnology*; vol. 16; pp. 17-26.

Jin, B.R. et al.; "Production Kinetics and Stability of a Transfectoma Cell Line Secreting Murine/Human Chimeric Antibody"; 1993; *Mol. Cells*; vol. 3; pp. 233-237.

Kadouri, A. et al.; "Dynamic Changes in Cytokine Secretion by Stromal Cells During Prolonged Maintenance Under Protein-Free Conditions"; 1992; *International Journal of Cell Cloning*; vol. 10; pp. 299-308.

Katinger, H. et al.; "Long-Term Stability of Continuously Perfused Animal Cells Immobilized on Novel Macroporous Microcarriers"; 1996; *Adv. Molecul. Cell Biol.*; vol. 15A; pp. 193-207.

Katsuta, H. et al.; "Effects of Polyamines on the Proliferation of Mammalian Cells in Tissue Culture"; 1975; *The Japanese Journal of Experimental Medicine*; vol. 45(5); pp. 345-354.

Katsuta, H. and Takaoka, T.; "Amino Acid Requirements of a Substrain of Strain L Cells (Mouse Fibroblasts) in Protein-Free Chemically Defined Synthetic Media"; 1960; *Japan. J. Exp. Med.*; vol. 30; pp. 235-259.

Kaufman, K. et al.; "Effect of von Willebrand Factor Coexpression on the Synthesis and Secretion of Factor VIII in Chinese Hamster Ovary Cells"; 1989; *Molecul. Cellul. Biol.*; vol. 9(3); pp. 1233-1242.

Keay, L.; "Autoclavable Low Cost Serum-Free Cell Culture Media: the Growth of Established Cell Lines and Production of Viruses"; 1976; *Biotechnology and Bioengineering*; vol. XVIII; pp. 363-382.

Keay, L.; "Autoclavable Low Cost Serum-Free Cell Culture Media. The Growth of L Cells and BHK Cells on Peptones"; 1975; *Biotechnology and Bioengineering*; vol. XVII; pp. 745-764.

Keen, M.J. and Rapson, N.T.; "Development of a Serum-Free Culture Medium for the Large Scale Production of Recombinant Protein From a Chinese Hamster Ovary Cell Line"; 1995; *Cytotechnology*; vol. 17; pp. 153-163.

Kim, S.J. et al.; "Characterization of Chimeric Antibody Producing CHO Cells in the Course of Dihydrofolate Reductase-Mediated Gene Amplification and Their Stability in the Absence of Selective Pressure"; Apr. 5, 1998; *Biotechnology and Bioengineering*; vol. 58(1); pp. 73-84.

Kim, N.S. et al.; "Clonal Variability Within Dihydrofolate Reductase-Mediated Gene Amplified Chinese Hamster Ovary Cells: Stability in the Absence of Selective Pressure"; Dec. 20, 1998; *Biotechnology and Bioengineering*; vol. 60(6); pp.679-688.

Kwon, M.S. et al.; "Use of Plant-Derived Protein Hydrolysates for Enhancing Growth of *Bombyx mori* (Silkworm) Insect Cells in Suspension Culture"; 2005; *Biotechnology and Applied Biochemistry*; vol. 42; pp. 1-7.

Lee, K.H. et al.; "Deregulated Expression of Cloned Transcription Factor E2F-1 in Chinese Hamster Ovary Cells Shifts Protein Patterns and Achtivates Growth in Protein-Free Medium"; 1996; *Biotechnol. Bioeng.*; vol. 50; pp. 273-279.

Luchette, C. et al.; "Isolation and Characterization of a CHO Cell Line Expressing rhFSH in Low Protein and Protein-Free Media"; 1997; *Animal Cell Technology*; pp. 669-674.

Merten, O.-W. et al.; "Production of Influenza Virus in Serum-Free Mammalian Cell Cultures"; 1999; *Dev. Biol. Stand.*; vol. 98; pp. 23-37.

Merten, O.-W. et al.; "The New Medium MDSS2N, Free of Any Animal Protein Supports Cell Growth and Production of Various Viruses"; 1999; *Cytotechnology*; vol. 30; pp. 191-201.

Merten, O.-W.; "Safety Issues of Animal Products Used in Serum-Free Media"; 1999; *Dev. Biol. Stand.*; vol. 99; pp. 167-180.

Miyaji, H. et al.; "Efficient Expression of Human Beta-interferon in Namalwa KJM-1 Cells Adapted to Serum-free Medium by a dhfr Gene Coamplification Method"; 1990; *Cytotechnology*; vol. 4; pp. 173-180.

Miyaji, H. et al.; "Expression of Human Beta-interferon in Namalwa KJM-1 Which Was Adapted to Serum-free Medium";1990; *Cytotechnology*; vol. 37; pp. 133-140.

Motz, M. et al.; "Expression of the Epstein-Barr Virus Major Membrane Proteins in Chinese Hamster Ovary Cells"; 1986; *Gene*; vol. 44(2-3); pp. 353-359; Abstract, 1 page.

Murhammer, D.W. and Gooche, C.F.; "Structural Features of Nonionic Polyglycol Polymer Molecules Responsible for the Protective Effect in Sparged Animal Cell Bioreactors"; 1990; *Biotechnol. Prog.*; vol. 6; pp. 142-146.

Nilsson, K. et al.; "Microcarrier Culture of Recombinant Chinese Hamster Ovary Cells for Production of Human Immune Interferon and Human Tissue-Type Plasminogen Activator"; 1988; *Appl. Microbiol. Biotechnol.*; vol. 27; pp. 366-371.

Nyberg, G.B. et al.; "Metabolism of Peptide Amino Acids by Chinese Hamster Ovary Cells Grown in a Complex Medium"; Feb. 5, 1999; *Biotechnology and Bioengineering*; vol. 62(3); pp. 324-335.

Ochiai, M. et al.; "Endotoxin Content in *Haemophilus influenzae* Type b Vaccine"; 2004; *Jpn. J. Infect. Dis.*; vol. 57; pp. 58-59.

Ogata, M. et al.; "High-Level Expression of Recombinant Human Soluble Thrombomodulin in serum-Free Medium by CHO-K1 Cells"; 1993; *Appl. Microbiol. Biotechnol.*; vol. 38; pp. 520-525.

Pak, S.C.O. et al.; "Super-CHO—A cell Line Capable of Autocrine Growth Under Fully Defined Protein-Free Conditions"; 1996; *Cytotechnology*; vol. 22; pp. 139-146.

Paterson, T. et al.; "Approaches to Maximizing Stable Expression of α1-Antitrypsin in Transformed CHO Cells"; 1994; *Appl. Microbiol. Biotechnol.*; vol. 40; pp. 691-698.

Pu, H. et al.; "Rapid Establishment of High-Producing Cell Lines Using Dicistronic Vectors with Glutamine Synthetase as the Selection Marker"; 1998; *Molecular Biotechnology*; vol. 10; pp. 17-25.

Qi, Y.M. et al.; "Evaluation of a Simple Protein Free Medium That Supports High Levels of Monoclonal Antibody Production"; 1996; *Cytotechnology*; vol. 21; pp. 95-109.

Rasmussen, B. et al.; "Isolation, Characterization and Recombinant Protein Expression in Veggie-CHO: A Serum-Free CHO Host Cell Line"; 1998; *Cytotechnology*; vol. 28; pp. 31-42.

Reiter, M. et al.; "Flow Cytometry and Two-Dimensional Electrophoresis (2-DE) for System Evaluation of Long Term Continuous Perused Animal Cell Cultures in Macroporous Beads"; 1992; *Cytotechnology*; vol. 9; pp. 247-253.

Renner, W.A. et al.; "Recombinant Cyclin E Expression Activates Proliferation and Obviates Surface Attachment of Chinese Hamster Ovary (CHO) Cells in Protein-Free Medium"; Aug. 1995; *Biotechnology and Bioengineering*; vol. 47; pp. 476-482.

Ryll, T. et al.; "Production of Recombinant Human Interleukin-2 with BHK Cells in a Hollow Fibre and a Stirred Tank Reactor with Protein-Free Medium"; 1990; *Journal of Biotechnology*; vol. 14; pp. 377-392.

Scharfenberg, K. and Wagner, R.; "A Reliable Strategy for the Achievement of Cell Lines Growing in Protein-Free Medium"; 1995; *Animal Cell Technology: Developments towards the 21$^{st}$ Century*; pp. 619-623.

Schlaeger, E.J.; "The Protein Hydrolystate, Primatone RL, is a Cost-Effective Multiple Growth Promoter of Mammalian Cell Culture in Serum-Containing and Serum-Free Media and Displays Anti-apoptosis Properties"; 1996; *Journal of Immunological Methods*; vol. 194; pp. 191-199.

Schlokat, U. et al.; "Herstellung und Charakterisierung von rekombinantem von Willebrand-Faktor zur Therapeutischen Anwendung"; 1995; *26th Hämophilie-Symposium Hamburg*; pp. 147-158.

Schlokat, U. et al.; "Production of Highly Homogeneous and Structurally Intact Recombinant von Willebrand Factor Multimers by Furin-Mediated Propeptide Removal in vitro"; 1996; *Biotechnol. Appl. Biochem.*; vol. 24; pp. 257-267.

Schneider, Y.-J.; "Optimisation of Hybridoma Cell Growth and Monoclonal Antibody Secretion in a Chemically Defined, Serum- and Protein-Free Sulture Medium"; 1989; *Journal of Immunological Methods*; vol. 116; pp. 65-77.

Sinacore, M.S. et al.; "CHO DUKX Cell Lineages Preadapted to Growth in Serum-Free Suspension Culture Enable Rapid Development of Cell Culture Processes for the Manufacture of Recombinant Proteins"; 1996; *Biotechnol. Bioeng.*; vol. 52; pp. 518-528.

Stoll, T.S. et al.; "Effects of Culture Conditions on the Production and Quality of Monoclonal IgA"; Aug. 15, 1997; *Enzyme and Microbial Technology*; vol. 21; pp. 203-211.

Sunstrom, N-A. et al.; "Recombinant Insulin-like Growth Factor-I (IGF-I) Production in *Super*-CHO Results in the Expression of IGF-I Receptor and IGF Binding Protein 3"; 1998; *Cytotechnology*; vol. 28; pp. 91-99.

Takahashi, M. et al.; "Production of Murine Monoclonal Antibodies in Protein Free Medium"; 1997; *Animal Cell Technology: Basic & Applied Aspects*; vol. 8; pp. 167-171.

Taylor, W.G. et al.; "Studies on a Serum Substitute for Mammalian Cells in Culture. I. Biological Efficacy of Whole and Fractionated Peptone Dialysate (36086)"; 1972; *Proc. Soc. Exp. Biol. Med.*; vol. 139; pp. 96-99.

Tecce, M.F. and Terrana, B.; "High Yield and High-Degree Purification of Human α-Fetoprotein Produced by Adaptation of the Human Hepatoma Cell Line HEP G2 in a Serum-Free Medium"; 1988; *Analytical Biochemistry*; vol. 169; pp. 306-311.

Teige et al.; 1994; *Journal of Biotechnology*; vol. 34; pp. 101-105.

Yamauchi, T. et al.; "Production of Human Antithrombin-III in a Serum-Free Culture of CHO Cells"; 1992; *Biosci. Biotech. Biochem.*; vol. 56(4); pp. 600-604.

Yin et al.; 1994; *Cell Biology International*; vol. 18(1); pp. 39-46.

Zang, M. et al.; "Production of Recombinant Proteins in Chinese Hamster Ovary Cells Using a Protein-Free Cell Culture Medium"; 1995; *Biotechnology*; vol. 13; pp. 389-392.

Zang-Gandor, M.O.; "Improved Transfection of CHO Cells Using Endotoxin-Free Plasmid DNA"; *Quiagen News*; 1997; vol. 4; pp. 1, 16-18.

BD Bionutrients™; Technical Manual Advanced Bioprocessing Third Edition Revised Oct. 2006, pp. 1-67.

Biochrom AG; Dulbecco's MEM (DMEM) Formulation Information, 1 page.

Biochrom AG; Dulbecco's MEM Formulation Information (German Version), 1 page.
Biochrom AG; HAM's F-12 Medium Formulation Information, 1 page.
Biochrom AG; ISCOVE's Medium Formulation Information (German Version), 1 page.
Biochrom AG; RPMI 1640 Medium Formulation Information (German Version), 1 page.
Biochrom AG; Dulbecco's MEM/HAM's F12 (1:1) Formulation Information (German Version), 1 page.
Cambrex; Classical Media Formulations, specifically MEM Product Information, 1 page.
Deltown Specialties; Peptone Selection Guide for Diagnostic and Fermentation Nutrients, 1994, 4 pages.
Extract from Hauser, H. and Wagner, R. eds.; *Mammalian Cell Biotechnology in Protein Production*; 1997; Walter de Gruyter, Berlin; pp. 33-137.
Extract form Quest International; "Sheffield Series" Products Catalogue, 13 pages.
Kerry Bio-Science; Pharma Ingredients Site for Hydrolysates, 4 pages.
Minutes of the Oral Proceedings to EP 99 939 251.7, 4 pages.
Page from the Quest International Technical Manual on Hydrolysates, 1988.
Product Information Bacto™ TC Yeastolate TC Yeastolate, UF, 2 pages.
Quest International; "Protein Derived Peptide Mixtures can Effectively Replace Serum, Glutamine and Other Free Amino Acids in Cell Culture Media"; Nov. 1998; Research Disclosure; pp. 1474-1476.
Quest International; Bioproducts Group HY-SOY® Product Information, 1995, 1 page.
Quest International; Bioproducts Group HY-SOY®, Product Information, 1998, 2 pages.
Quest International; HyPep® 1510 (IPL:5Z10493) Product Information, 2 pages.
Quest International; Pharma Ingredients Site with Product Information for HyPep® 1510 and Hy-Soy®, 11 pages.
Quest International; Product Informatiion; www.sheffield-products.com; accessed on Nov. 18, 2003; 14 pages.
SAFC Biosciences™; Dulbecco's Modified Eagles's Medium/Ham's Nutrient Mixture F12 Product Information, 2006, 2 pages.
SAFC Biosciences™; RPMI 1640 Medium Modified Product Information, 2006, 2 pages.
Sigma®; Biochemicals Organic Compounds Diagnostic Reagents Catalogue, 1995, 6 pages.
Sigma-Aldrich; DME/Nutrient Mixture F12 Ham Product Information, 8 pages.
Sigma-Aldrich; Dulbecco's Modified Eagle's Medium (DME)/Ham's Nutrient Mixture F-12, Product Information, 2 pages.
Sigma-Aldrich; IPL-41 Insect Medium ProductInformation, 1 page.
Sigma-Aldrich; Minimum Essential Medium Eagle (MEM), ProductInformation, 6 pages.
Sigma-Aldrich; Minimum Essential Medium Eagle, Joklik Modification, Specification Sheet, 1 page.
Sigma-Aldrich; P1265 N-Z Soy Peptone Product Detail, 1 page.
Sigma-Aldrich; P6463 Peptone Hy-Soy® T Product Detail, 1 page.
AstraZeneca AB Opposition Brief to European Patent No. 1200561 dated Mar. 14, 2007.
Bayer Healthcare AG Opposition Brief to European Patent No. 1200561 dated Mar. 13, 2007.
Bioceuticals Arzneimittel AG Opposition Brief to European Patent No. 1200561 dated Mar. 14, 2007.
Biogen IDEC MA, Inc. Opposition Brief to European Patent No. 1200561 dated Mar. 14, 2007.
Campina Nederland Holding B.V. Opposition Brief to European Patent No. 1220893 dated Mar. 21, 2007.
F. Hoffmann-La Roche AG Opposition Brief to European Patent No. 1200561 dated Mar. 13, 2007.
F. Hoffmann-La Roche AG Opposition Brief to European Patent No. 1220893 dated Mar. 27, 2007.
Kerry Ingredients (UK) Limited Opposition Brief to European Patent No. 1220893 dated Mar. 21, 2007.
Maxygen Inc. Opposition Brief to European Patent No. 1200561 dated Mar. 14, 2007.
Maxygen, Inc. Opposition Brief to European Patent No. 1220893 dated Mar. 20, 2007.
Declaration of Dr. Ricardo Matanguihan in support of Maxygen, Inc. Opposition Brief to European Patent No. 1220893 dated Mar. 20, 2007 (including Annexes A and B).
Declaration of Dr. Ruediger Heidemann in support of Maxygen, Inc. Opposition Brief to European Patent No. 1220893 dated Mar. 20, 2007 (including Annexes A-F).
Merck Serono International S.A. Opposition Brief to European Patent No. 1200561 dated Mar. 12, 2007.
Merck Serono International S.A. Opposition Brief to European Patent No. 1220893 dated Mar. 20, 2007.
N.V. Organon Opposition Brief to European Patent No. 1200561 dated Mar. 14, 2007.
Novartis AG Opposition Brief to European Patent No. 1200561 dated Mar. 14, 2007.
Novartis AG Opposition Brief to European Patent No. 1220893 dated Mar. 21, 2007.
Novo Nordisk A/S Opposition Brief to European Patent No. 1200561 dated Mar. 14, 2007.
Novo Nordisk A/S Opposition Brief to European Patent No. 1220893 dated Mar. 21, 2007.
Sigma-Aldrich Co. Opposition Brief to European Patent No. 1220893 dated Mar. 21, 2007.
Wyeth Opposition Brief to European Patent No. 1200561 dated Mar. 14, 2007.
Werner et al.; "Safety and economic aspects of continuous mammalian cell culture"; *J. Biotechnol.*; 22:51-68 (1992).

RECOMBINANT CELL CLONES HAVING INCREASED STABILITY AND METHODS OF MAKING AND USING THE SAME

CROSS-REFERENCES TO RELATED APPLICATIONS

This application is a divisional of U.S. application Ser. No. 12/488,465, filed Jun. 19, 2009, which is a continuation of U.S. application Ser. No. 11/482,504 filed Jul. 7, 2006, which is a divisional of U.S. application Ser. No. 11/123,362 filed May 6, 2005, now U.S. Pat. No. 7,294,466, which is a continuation of U.S. application Ser. No. 10/170,661 filed Jun. 12, 2002, now U.S. Pat. No. 6,936,441, which is a continuation of U.S. application Ser. No. 09/324,612 filed Jun. 2, 1999, now U.S. Pat. No. 6,475,725, which is a continuation-in-part application of U.S. application Ser. No. 09/100,253 filed Jun. 19, 1998, now U.S. Pat. No. 6,100,061, all of which are herein incorporated by reference in their entirety for all purposes.

BACKGROUND OF THE INVENTION

The present invention relates to a stable recombinant cell clone that is stable for at least 40 generations in serum- and protein-free medium, a biomass obtained by multiplying the stable cell clone under serum- and protein-free culturing conditions, and a method of preparing recombinant proteins by means of the biomass. Furthermore, the invention relates to a method of recovering stable recombinant cell clones. Furthermore, the invention relates to the production of a recombinant protein in a serum- and protein-free synthetic minimum medium.

Another aspect of the invention is a serum- and protein-free medium for culturing cells expressing a recombinant protein.

The preparation of recombinant proteins, in particular of biomedical products, such as blood factors, is gaining in importance. To allow for an optimum growth of recombinant cells, serum is added to the medium in most instances. Because of the high costs of serum and for avoiding possible contamination's in the culturing medium by viral or molecular pathogens from the serum, a number of serum-free media have been developed which, in particular, should not contain any additives of bovine or human origin. In addition to the low risk of contaminating the prepared products with viral and molecular pathogens, the use of such media in the preparation process also allows for a simpler purification of the expressed proteins.

In most instances, recombinant cells are first cultured in serum-containing medium up to a high cell density, e.g. for a working cell bank, and subsequently they are re-adapted to serum-free medium during the production phase.

Miyaji et al., *Cytotechnology*, 3:133-140 (1990) selected serum-independent cell clones in serum-free medium which contained insulin and transferrin. However, the living cell number and the expression rate proved to decrease continuously after 16 days. By co-amplification with a labeling gene, Mayaji et al., *Cytotechnology*, 4:173-180 (1990) tried to improve the expression rate and the productivity of the recombinant, cells.

Yamaguchi et al., *Biosci. Biotechnol. Biochem.*, 56:600-604 (1992) established serum-independent recombinant CHO sub-clones by culturing serum-dependent cells on microtiter plates as monolayer for 3 to 4 weeks in serum-free medium that contained human serum albumin, insulin and transferrin. Approximately 0.1% of the cells were serum-independent. Part of the subclones also grew in suspension culture in serum-free medium, yet the cells aggregated and formed lumps. The duplicating time of the cells amounted to 1.5 days. Yet there are no data either on the stability of the serum-independent clones obtained, nor on the long time cultivation of these clones under serum-free conditions.

Media which allow for the maintenance of the metabolic activity and for a growth of cells during the serum-free phase frequently contain additional substances, e.g. growth factors, such as insulin or transferrin, or adherence factors which substitute the serum components.

To avoid the addition of polypeptide factors, such as insulin or transferrin, and to allow for protein free culturing conditions, various techniques have been developed. Thus, specifically defined, complete protein-free media have been developed which allow for a cell-growth also under protein-free conditions.

WO 97/05240 describes the preparation of recombinant proteins under protein-free conditions, the cells co-expressing a growth factor in addition to the desired protein.

P 2696001 describes the use of a protein-free medium for the production of factor VIII in CHO cells by adding a non-ionic surface-active agent or cyclodextrin to increase the productivity of the host cells. To increase the effectiveness of these additives, the addition of, e.g., butyrate and lithium is recommended. As indicated in the specification, the addition of pluronic F-68 results in a marked increase in cell numbers.

WO 96/26266 describes the culturing of cells in a medium which contains a glutamine-containing protein hydrolysate whose content of free amino acids is less than 15 k of the total weight of the protein, and whose peptides have a molecular weight of less than 44 kD. As the culturing medium for the cell cultures, a synthetic minimum medium is used as the basic medium to which, inter alia, fetal calf serum, gentamycin and mercaptoethanol are added in addition to protein hydrolysate. The use of this serum-containing medium for the recombinant production of blood factors has not been mentioned.

U.S. Pat. No. 5,393,668 describes special synthetic surfaces which allow for a growth of adherent cells under protein-free conditions.

To stimulate cell proliferation, CHO cells which overexpress human insulin have been multiplied on an artificial substrate to which insulin is covalently bound (Ito et al., *PNAS USA*, 93:3598-3601 (1996)).

EP 0 872 487 describes the preparation of recombinant factor VIII in protein-free medium containing recombinant insulin to which polyols are added. According to the specification, the addition of pluronic F-68 results in an increased factor VIII productivity of BHK cells, and the addition of iron ions yet enhances this rise in productivity.

Reiter et al., *Cytotechnology*, 9:247-253 (1992) describe the immobilization of r-CHO cells first grown in serum-containing medium at a high density on carriers, and subsequent perfusion of the immobilized cells in protein-free medium during the production phase, wherein a continuous liberation of protein into the cell culture supernatant was found. There, the cells were perfused for less than 10 generations in protein-free medium.

Katinger et al., *Adv. In Mol. Cell Biol.*, 15a:193-207 (1996) describe the preparation of stable cell cultures wherein the cells are immobilized on macroporous carriers. It is emphasized that perfusion cultures with porous carrier materials would be preferable to other methods. Stable clones expressing recombinant proteins, such as FVIII or von-Willebrand factor, are not described, the cells are invariably grown first in serum-containing medium and are only later transferred to serum- and protein-free medium.

Previous methods for the successful preparation of a large-scale cell culture under protein-free conditions have been described for continuous cell lines, in particular VERO cells (see, e.g., WO 96/15231). There, the cells are grown under serum- and protein-free conditions from the original ampule up to a large technical scale of 1200 l. However, these are not recombinant cells, but host cells which are used for the production of virus antigen in a lytic process.

In contrast to adherent VERO cells, e.g. CHO cells are dependent on adhesion to a limited extent only. CHO cells grown by means of conventional methods under serum-containing conditions are capable of binding both to smooth and to porous micro-carriers (U.S. Pat. No. 4,978,616; Reiter et al., *Cytotechnology,* 9:247-253 (1992)). If CHO cells are grown under serum-free conditions, they lose this property and do not adhere to smooth carriers, such as, e.g., Cytodex 3, or they detach easily therefrom, unless adherence-promoting additives, such as, e.g., fibronectin, are put into the medium. Because of the slight adherence of CHO cells to carriers under serum-free conditions, the production of recombinant proteins thus mainly is effected in suspension culture. There, the production process may be effected as a continuous or as a batch-wise method. The recombinant cell culture at first is grown in a bioreactor up to an optimum cell density, optionally the protein expression is induced, and for harvesting, the medium containing the expressed proteins but also recombinant cells is withdrawn at certain intervals from the reaction tank and thus from the production process. By the continuous loss of biomass, the production efficiency in the bioreactor drops and increases again slowly only after the addition of fresh medium, since the cells must grow up to the desired cell density. Thus, despite the continuous process, repeatedly there is a phase of retardation, in which the production rate in this system drops. Furthermore, the growth and production capacity in such a system is limited by the maximum cell density attainable.

When adapting cells initially grown under serum containing conditions to protein-free medium, it has repeatedly been found that the yield of expressed protein and the productivity of recombinant CHO cells greatly drops after adaptation in protein-free medium as compared to serum-containing conditions (Paterson et al., *Appl. Microbiol. Biotechnol.,* 40:691-658 (1994)). This is the consequence of an instability or reduced growth of the recombinant clones due to the changed culturing conditions. Despite the use of a stable original clone, on account of the altered fermentation conditions, repeatedly a large portion of the cells become cells with reduced expression or also non-producers, which overgrow product producers during the production process, whereby the fermented culture finally largely consists of non-producers or of such cells having a low expression.

As a consequence, the maximum production capacity of the fermentation culture drops continuously, and a maximum product production is restricted to a certain number of generations or cell passages.

Thus, there is a need for a system in which a continuous production is possible over as long a period of time as possible, in particular in the large-scale production of recombinant proteins under serum- and protein-free conditions.

It would furthermore be desirable to obtain a recombinant cell clone which is stable in the production phase for many generations under protein free conditions and which expresses recombinant protein.

BRIEF SUMMARY OF THE INVENTION

It is the object of the present invention to provide an efficient method of preparing recombinant proteins under serum- and protein-free cultivation and production conditions.

It is a further object to provide a stable recombinant cell clone.

It is another object of the present invention to achieve an increase in productivity of a recombinant cell clone by using a protein- and serum-free medium.

BRIEF DESCRIPTION OF THE DRAWINGS

a) F VIII-activity (mUnits/ml) and perfusion rate (1-5 day) over a period of 42 days.

b) Volumetric productivity (units factor VIII/l/day) in the perfusion bioreactor.

DETAILED DESCRIPTION OF THE INVENTION

It is the object of the present invention to provide an efficient method of preparing recombinant proteins under serum- and protein-free cultivation and production conditions.

It is a further object to provide a stable recombinant cell clone.

It is another object of the present invention to achieve an increase in productivity of a recombinant cell clone by using a protein- and serum-free medium.

According to the invention, this object is achieved by providing a recombinant cell clone obtainable from a cell culture that is obtained after culturing a recombinant original cell clone on serum-containing medium and re-adapting the cells to serum- and protein free medium. The cells are continued to be cultured in serum- and protein-free medium under production equivalent conditions for at least 40 generations.

Preferably, culturing of the cells is effected without selection for the selection labeling and/or amplification gene, e.g. in the absence of MTX in case of CHO-dhfr$^-$ cells.

By original cell clone within the scope of this invention a recombinant cell clone transfectant is understood which, upon transfection of host cells with a recombinant nucleotide sequence, expresses recombinant product in a stable manner under laboratory conditions. To optimize growth, the original clone is first grown in serum-containing medium. To increase the productivity, the original clone optionally is first grown in the presence of a selecting agent and selection for the selection marker and/or amplification marker. For the large-scale production, the original cell clone is first grown under serum-containing culturing conditions up to a high cell density, and shortly before the production phase it is re-adapted to serum- and/or protein-free medium. In this case, culturing is preferably effected without selection pressure.

In another preferred embodiment the recombinant original cell clone may be cultivated in serum- and protein-free medium already from the beginning, rendering re-adaptation unnecessary. Optionally, a selecting agent may also be used in this case, and selection may be for the selection and/or amplification marker. A respective method is, e.g., described in EP 0 711 835.

It has been found that under these conditions, a large part of more than 95% of the cells become nonproduct producers in such a cell culture which has been re-adapted to serum- and protein free medium. By means of immune fluorescence with product-specific antibodies it could be shown that in dependence on the generation time of the cells in serum- and protein-free medium, the number of the non-producers rises in a culture and overgrows the product-producers, whereby the production capacity of the culture decreases.

The cell culture obtained after re-adaptation to serum- and protein free medium is assayed for those cell clones of the cell population which are producers of the stable product under serum- and protein-free conditions, optionally in the absence of a selection pressure. This may be effected, e.g., by means of immunofluorescence with labeled antibodies specifically directed against the recombinant polypeptide or protein. Those cells which have been identified as product producers are isolated from the cell culture and again multiplied under serum- and protein-free, optionally under production-equivalent, conditions. Isolation of the cells may be effected by isolating the cells and assaying for product-producers. Optimally, the cell culture containing the stable cells is again assayed for stable recombinant clones, and the latter are isolated from the cell culture and cloned. Subsequently, the stable recombinant cell clones obtained under serum- and protein-free conditions are further multiplied under serum- and protein-free conditions.

The recombinant cell clone according to the invention is characterized in that it is stable in serum-free and protein-free medium for at least 40, preferably at least 50, in particular more than 60 generations and expresses recombinant product.

According to a particular aspect of the invention, the stable recombinant cell clone is present in isolated form. Departing from the stable cell clone, a cell culture is obtained under serum- and protein-free conditions by multiplying the stable cells.

The stable recombinant cell clone of the invention preferably is derived from a recombinant mammalian cell. The recombinant mammalian cells may be all cells that contain sequences which encode a recombinant polypeptide or protein. Included are all continuously growing cells which grow adherently and non-adherently. Particularly preferred are recombinant CHO cells or BHK cells. Recombinant polypeptides or proteins may be blood factors, growth factors or other biomedically relevant products.

According to the present invention, stable recombinant cell clones are preferred which contain the encoding sequence for a recombinant blood factor, such as factor II, factor V, factor VII, factor VIII, factor IX, factor X, factor XI, protein S, protein C, an activated form of any one of these factors, or VWF, and which are capable of stable expression of this factor over several generations. Particularly preferred are recombinant CHO cells, which express VWF or a polypeptide having VWF activity, factor VIII or a polypeptide having factor VIII activity, VWF and factor VIII, factor IX or factor II.

The cell clone of the invention selected under serum and protein-free conditions is particularly characterized in that it is stable in serum and protein-free medium for at least 40, preferably for at least 50 generations, particularly preferred for more than 60 generations.

To provide a master cell bank, 30 generations are required. To carry out an average batch culture on a 1,000 liter scale, at least approximately 40 generations are required. Thus it has become possible for the first time to prepare with one individual clone a master cell bank (MCB), a working cell bank (WCB) including approximately 8 to 10 generations and thus, a production-scale cell culture (production biomass) with up to 20 to 25 generations under these conditions, since so far cell clones have become unstable after having grown on serum- or protein-free medium for some generations, or have exhibited a reduced viability, whereby a) no uniform cell culture with product producers, and b) no stable product productivity has been possible over an extended period of time.

The cell clone according to the invention thus is stable and productive for at least 40 generations under production conditions in serum and protein-free medium. Previously described methods merely exhibited a product productivity for a generation number of less than 10 generations under protein-free conditions (Reiter et al., (1992) *supra*).

The criterion for stability is held to be a minimum number of at least 40 generations, preferably more than 50 generations, particularly preferred more than 60 generations in the production process, during which a stable expression of the proteins takes place and the cells do not exhibit any tumorigenic properties.

Surprisingly it has been found that the cell clone according to the invention exhibits an increased product productivity under serum and protein-free conditions even in comparison to the original cell clone which had been cultured in serum containing medium.

In addition, it has surprisingly been found that the productivity of the cultivated cells may be increased by adding additional amino acids and/or purified, ultrafiltrated soybean peptone to the serum- and protein-free medium. In this case, the increase in productivity is not caused by the enhanced cell growth rate; rather, the culture conditions directly influence the productivity of the cells expressing a recombinant protein.

A particular aspect is the use of a protein- and serum-free medium to which a mixture of amino acids selected from the group of L-asparagine, L-cysteine, L-cystine, L-proline, L-tryptophan and L-glutamine has been added.

The amino acids may be added to the medium individually or in combination.

Particularly preferred is the combined addition of all the amino acids listed in this group, i.e. L-asparagine, L-cysteine, L-cystine, L-proline, L-tryptophan and L-glutamine.

The increase in productivity by the addition of the amino acid mixture, which may be thus achieved, was particularly surprising because the synthetic minimum media as described in the prior art, e.g. DMEM/HAM's F12, already contain low concentrations of amino acids.

According to a further aspect, the present invention provides a cell culture containing at least 90%, preferably more than 95%, particularly preferred more than 98%, stable recombinant cells which are stable under serum- and protein-free conditions for at least 40 generations, in particular for at least 50 generations, and express recombinant product.

Within the scope of the present invention, by cell culture a master cell bank (MCB), a working cell bank (WCB) or a production biomass in a large-technical production bioreactor is understood.

According to the invention, the cell culture is particularly obtained by culturing a stable recombinant cell clone of the above-defined kind under serum and protein-free conditions.

The cell culture of the invention is obtainable by multiplying the isolated stable cell clone from the individual clone, the seed cells up to the MCB, the WCB or a biomass on a production scale in the bioreactor under serum and protein-free conditions, preferably without selection pressure on the selection and/or marker gene. In particular, it has been shown that the recombinant cells in a cell culture which are obtained departing from the stable recombinant clone of the invention are stable under serum- and protein-free conditions for at least 40 generations.

The cell culture provided according to the present invention, which has been prepared from a serum and protein-independent stable cell clone, exhibits at least 90%, preferably at least 95%, particularly preferred at least 98%, stable recombinant cells under protein-free culturing and production conditions. By stable recombinant cells, in particular recombinant mammalian cells are understood which are derived from the stable cell clone. Preferred are recombinant CHO cells, preferably CHO-dhfr⁻ cells, CHO-K1 cells and BHK cells that express a blood factor, preferably recombinant vWF, factor VII, factor VIII and vWF, factor IX or factor II.

The cell culture according to the invention may contain the stable recombinant cells in the form of a suspension culture. The cells may also be immobilized on a carrier, in particular on a microcarrier, porous microcarriers being particularly preferred. Porous carriers, such as e.g. Cytoline® or Cytopore® have proved to be particularly suitable.

According to a further aspect, the present invention provides a method for the large-technical production of a recombinant product under serum and protein-free conditions, by using the stable cell clone according to the invention. The method comprises the steps of providing an isolated, stable recombinant cell clone of the above-defined kind for producing a cell culture. Multiplication of the isolated stable cell clone is effected from the stable individual cell clone up to the cell culture under serum and protein-free conditions. In particular, also sub-culturing of the stable cell clones is effected under protein-free conditions, in particular without the addition of a protease, such as, e.g., trypsin. Thus it is ensured that at no time during the production of a cell culture used in the production of a recombinant product, a contamination occurs which possibly could be caused by the addition of serum or protein-containing additives of human or animal origin to the cell culture. Thus, for the first time a method is described which allows for working under serum- and protein-free conditions, starting from the original clone, via the preparation of a working cell bank as far as to the production biomass and the subsequent production of recombinant protein.

The preparation of the recombinant products with the cell culture of the invention which contains more than 90%, preferably more than 95%, particularly preferred more than 98%, of stable product producer cells, may be effected as a suspension culture or with cells immobilized on carriers. The process may be effected as a batch-wise or a continuous method or by means of perfusion technique with serum and protein free medium.

Moreover, the culturing process may be effected by means of the chemostat method as extensively described in prior art (Werner et al., *J. Biotechnol.*, 22:51-68 (1992)). For example, a stirred bioreactor or an airlift reactor may be used.

The expressed recombinant proteins are then recovered from the cell culture supernatant, purified by means of methods known from the prior art, and further processed.

Any known synthetic medium can be used as the serum and protein-free medium. Conventional synthetic minimum media may contain inorganic salts, amino acids, vitamins and a carbohydrate source and water. It may, e.g., be DMEM/HAM's F-12 medium. The content of soybean or yeast extract may range between 0.1 and 100 g/l, particularly preferred between 1 and 5 g/l. As a particularly preferred embodiment, soybean extract, e.g. soybean peptone, may be used. The molecular weight of the soybean peptone can be less than 50 kD, preferably less than 10 kD.

The addition of ultrafiltrated soybean peptone having an average molecular weight of 350 Dalton has proven particularly advantageous for the productivity of the recombinant cell lines. It is a soybean isolate having a total nitrogen content of about 9.5% and a free amino acid content of about 13%.

Particularly preferred is the use of a purified, ultrafiltrated soybean peptone having a molecular weight of $\leq 1000$ Dalton, preferably $\leq 500$ Dalton, particularly preferably $\leq 350$ Dalton.

Ultrafiltration may be effected by means of methods extensively described in prior art, e.g., using membrane filters with a defined cut-off.

The ultrafiltration soybean peptone may be purified by means of gel chromatography, for example using Sephadex chromatography, e.g., Sephadex G25 or Sephadex G10 or equivalent materials; ion exchange chromatography, or size exclusion chromatography or reversed phase chromatography. These are methods well known to a skilled artisan from prior art.

Particularly preferably a medium having the following composition is used: synthetic minimum medium (1 to 25 g/l) soybean peptone (0.5 to 50 g/l), L-glutamine (0.05 to 1 g/l), NaHCO$_3$ (0.1 to 10 g/l), ascorbic acid (0.0005 to 0.05 g/l), ethanol amine (0.0005 to 0.05), Na selenite (1 to 15 µg/l). Optionally, a non-ionic surface-active agent, such as, e.g., polypropylene glycol (PLURONIC F-61, PLURONIC F-68, SYNPERONIC F-68, PLURONIC F-71, or PLURONIC F-108) maybe added to the medium as a defoaming agent. This agent is generally applied to protect the cells from the negative effects of aeration, since without the addition of a surface-active agent, the rising and bursting air bubbles may damage those cells which are at the surface of these air bubbles ("sparging"). (See, e.g., Murhammer and Goochee, *Biotechnol. Prog.*, 6:142148 (1990)).

The amount of non-ionic surface-active agent may range between 0.05 and 10 g/l, particularly preferred is as low an amount as possible, between 0.1 and 5 g/l. Furthermore, the medium may also contain cyclodextrine or a derivative thereof. The addition of non-ionic surface-active agent or of cyclodextrine is, however, not essential to the invention. Preferably, the serum and protein-free medium contains a protease inhibitor, such as, e.g., serine protease inhibitors, which are suitable for tissue culture and which are of synthetic or vegetable origin.

In another preferred embodiment the following amino acid mixture is additionally added to the above-mentioned medium: L-asparagine (0.001 to 1 g/l; preferably 0.01 to 0.05 g/l; particularly preferably 0.015 to 0.03 g/l), L-cysteine (0.001 to 1 g/l; preferably 0.005 to 0.05 g/l; particularly preferably 0.01 to 0.03 g/l), L-cystine (0.001 to 1 g/l; preferably 0.01 to 0.05 g/l; particularly preferably 0.015 to 0.03 g/l). L-proline (0.001 to 1.5 g/l; preferably 0.01 to 0.07 g/l; particularly preferably 0.02 to 0.05 g/l), L-tryptophan (0.001 to 1 g/l; preferably 0.01 to 0.05 g/l; particularly preferably 0.015 to 0.03 g/l) and L-glutamine (0.05 to 10 g/l; preferably 0.1 to 1 g/l). The above-mentioned amino acids may be added to the medium individually or in combination. Particularly preferred is the combined addition of the amino acid mixture containing all of the above-mentioned amino acids.

In a particular embodiment a serum- and protein-free medium is used additionally containing a combination of the above-mentioned amino acid mixtures and purified, ultrafiltrated soybean peptone.

Surprisingly, it has proven possible to heat the medium to 70 to 95° C., preferably 85 to 95° C., for about 5 to 20 minutes, preferably 15 minutes, without causing negative effects, e.g., in order to inactivate viruses or other pathogens.

The parameters for culturing the cells, such as O$_2$ concentration, perfusion rate or medium exchange, pH, temperature and culturing technique will depend on the individual cell types used and may be determined by the skilled artisan in a simple manner. For instance, culturing of CHO cells may be effected in a stirring tank and under perfusion with protein-free medium at a perfusion rate of from 2 to 10 volume exchanges/day, at a pH of between 7.0 and 7.8, preferably at 7.4, and an $O_2$ concentration of between 40% up to 60%, preferably at 50%, and at a temperature of between 34° and 38°, preferably of 37°.

Moreover, the cells may also be cultured by means of the chemostat method, using a pH of between 6.9 and 7.8, preferably 7.1, an $O_2$ concentration of between 10% and 60%, preferably 20%, and a dilution rate D of 0.25 to 1.0, preferably 0.5.

According to a further aspect, the present invention provides a method of recovering a stable recombinant cell clone, comprising the steps of
  multiplying a recombinant original clone up to the cell culture in serum-containing medium, preferably without selection pressure,
  culturing the cells under serum and protein-free, preferably under production equivalent, conditions,
  assaying the cell culture under serum and protein free conditions for product producers,
  cloning the stable recombinant cell clones under serum- and protein-free conditions, wherein cloning may be effected by generally known techniques, such as diluting out and growing the individual cell clones,
  multiplying the isolated cell clones under serum and protein-free conditions,
  and optionally assaying the cell culture for product producers.

Only those recombinant cell clones are considered stable which express recombinant protein in a stable manner in protein-free medium for at least 10, preferably at least 20, and in particular at least 50 generations.

According to a further aspect, the invention relates to a method of recovering a stable recombinant cell clone, comprising the steps of
  multiplying a non-recombinant starting cell or cell line under serum and protein-free conditions, and cloning a stable non-recombinant cell-clone under serum- and protein-free conditions,
  transfecting the stable cell clone with a recombinant nucleic acid and isolating stable recombinant cell clones,
  Culturing the stable cell clone transfectants in serum- and protein-free medium, optionally under production-equivalent conditions,
  assaying the stable recombinant cells for production and product stability.

A particularly preferred aspect of the present invention provides the preparation of a stable cell clone comprising the steps of
  multiplying a recombinant original clone up to the cell culture in serum- and protein-free medium, preferably without selection pressure;
  culturing the cells under serum- and protein-free, preferably under production-equivalent conditions,
  assaying the cell culture under serum- and protein-free conditions for product producers,
  cloning the stable recombinant cell clones under serum- and protein-free conditions, wherein cloning may be effected by generally known techniques, such as diluting out and growing the individual cell clones,
  multiplying the isolated cell clones under serum- and protein-free conditions, and
  optionally assaying the cell culture for product producers.

Only those recombinant cell clones are considered stable which express recombinant protein in a stable manner in protein-free medium for at least 10, preferably at least 20, and in particular at least 50 generations.

Also preferred is the use of a serum- and protein-free medium to increase the productivity of a cell clone expressing a recombinant protein to which additionally a defined amino acid mixture and/or purified, ultrafiltrated soybean peptone have been added.

The invention will be described in more detail by way of the following examples, as well as drawings to which, however, it shall not be restricted.

EXAMPLES

Example 1

Figure 1:
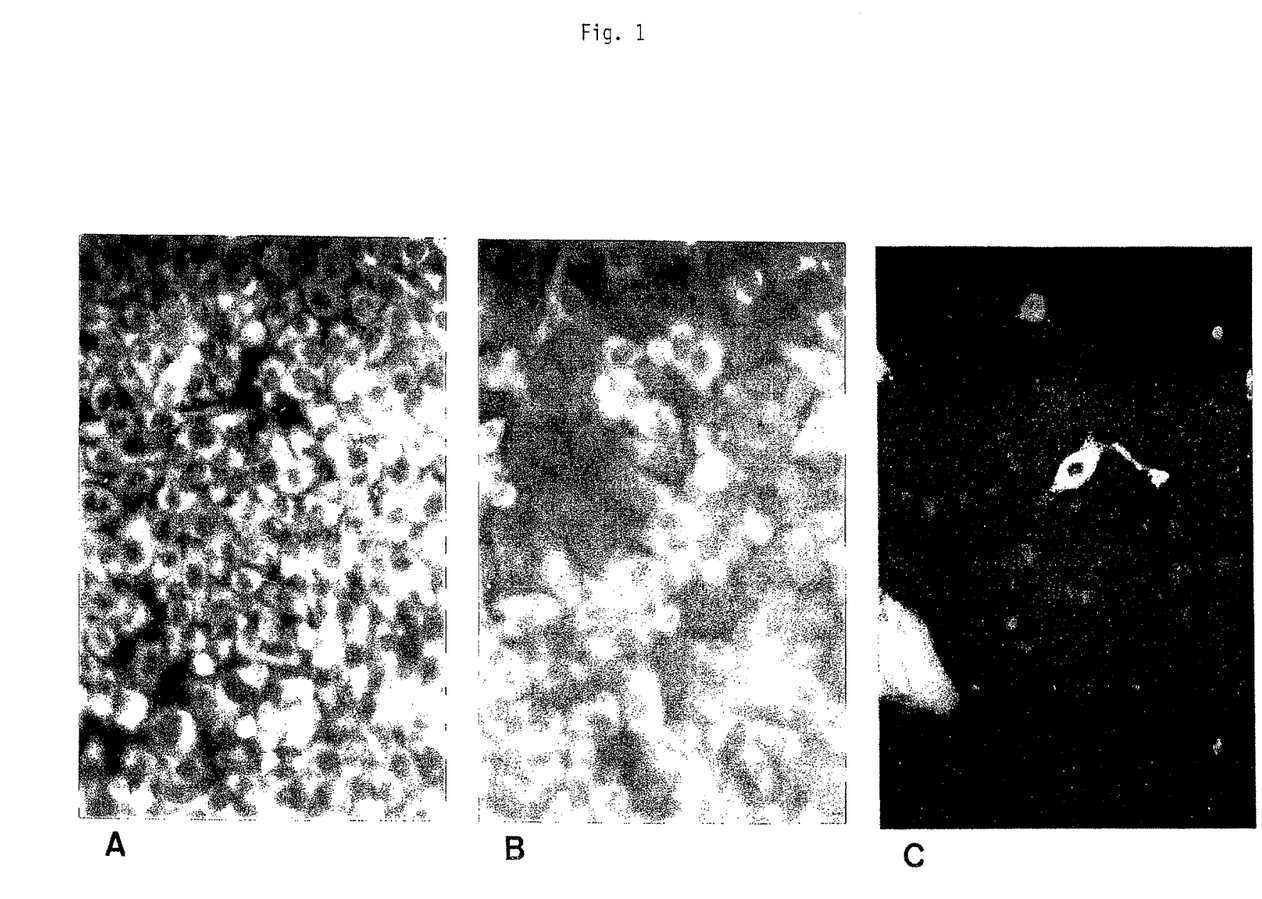
FIG. 1 shows the microscopy of a working cell bank of an original clone at the time of re-adaptation from serum-containing to serum- and protein-free medium (A), after 10 generations in serum- and protein-free medium (B), and after 60 generations in serum- and protein free medium (C).

Stability of rvWF-CHO Cells after Re-Adaptation from Serum-Containing to Serum- and Protein-Free Medium CHO-dhfr⁻ cells were co-transfected with plasmids phAct-rvWF and pSV-dhfr, and vWF-expressing clones, as described in Fischer et al., *FEBS Letters*, 351:345-348 (1994)) were sub-cloned. From those sub-clones which expressed rvWF in a stable manner, a working cell bank (WCB) was set up under serum-containing conditions, yet in the absence of MTX, and the cells were immobilized on a porous microcarrier (Cytopore®) under serum-containing conditions. When a cell density of $2\times10^7$ cells/ml carrier matrix had been reached, readaptation of the cells to serum- and protein-free medium was effected. The cells were continued to be cultured for several generations under serum- and protein-free conditions. By means of immunofluorescence with labeled anti-vWF antibodies, the cells were assayed in serum- and protein-free medium at different points of time. The evaluation of the stability of the cells of the working cell bank was effected prior to medium readaptation, after 10 and after 60 generations in serum- and protein-free medium. Whereas the working cell bank still had 100% rvWF producers (FIG. 1A), the portion of rvWF producers after 10 generations in serum- and protein-free medium had decreased to approximately 50% (FIG. 1B). After 60 generations, more than 95% of the cells were identified as non-producers (FIG. 1C).

Example 2

Cloning of Stable Recombinant CHO Clones

Figure 2:
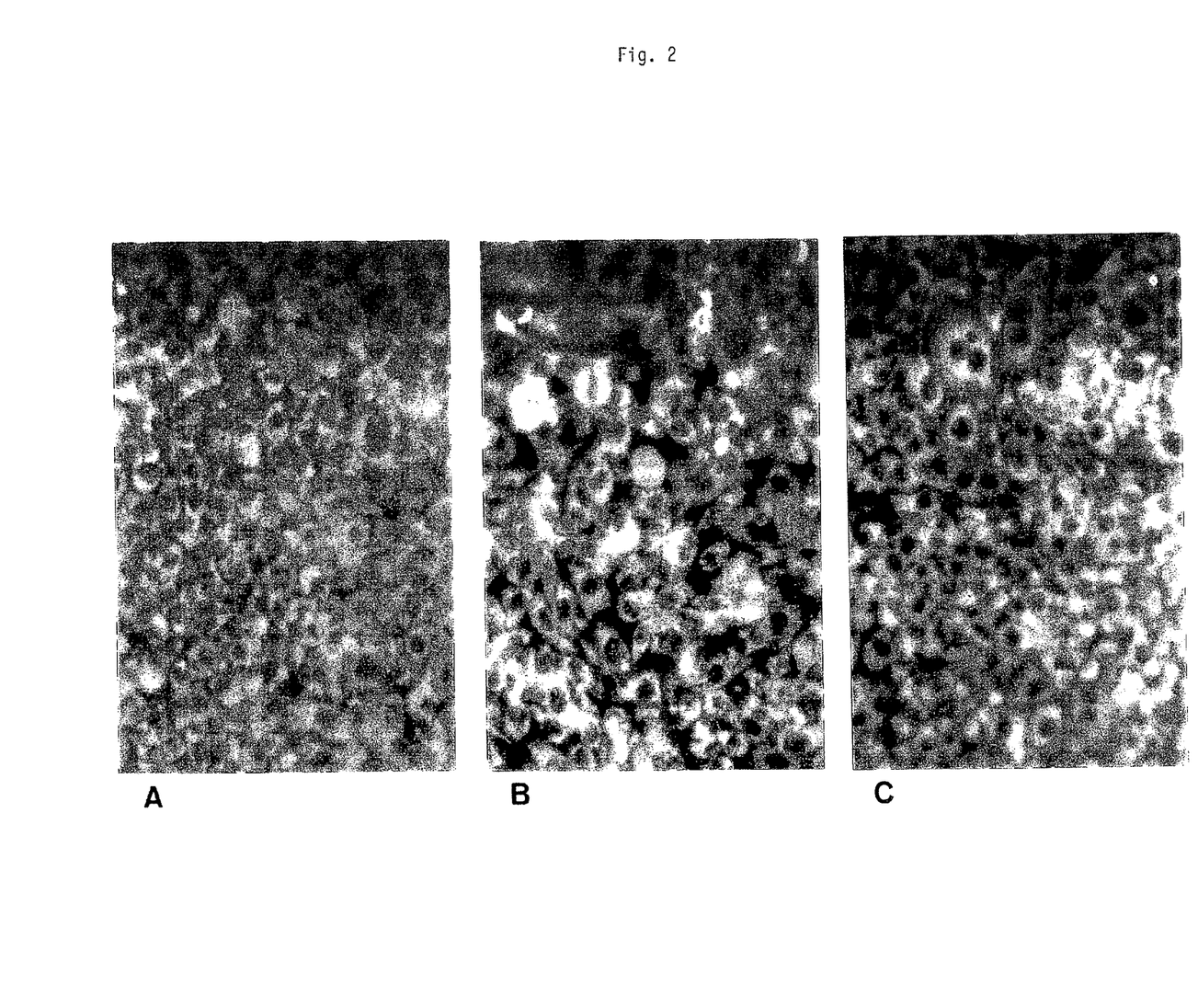
FIG. 2 shows the microscopy of a cell culture starting with a stable recombinant cell clone under serum- and protein-free conditions at the working cell bank stage (A), after 10 generations (B) and after 60 generations (C).

From the cell culture containing rvWF-CHO cells according to Example 1, (the stable cell clone designated r-vWF-CHO F7 was deposited on Jan. 22, 1998, at the European Collection of Cell Cultures (ECACC), Salisbury, Wilshire, SP4 0JG, UK, according to the Budapest Treaty, and received the deposit number 98012206) which had been cultured for 60 generations in serum- and protein-free medium (FIG. 1C), a dilution was made, and 0.1 cells/well were each seeded in a micro-titer plate. The cells were cultured for approximately 3 weeks in DMEM/HAM's F12 without serum or protein additions and without selection pressure, and the cells were assayed by means of immunofluorescence with labeled anti-vWF antibody. A cell clone that had been identified as positive was used as the starting clone for the preparation of a seed cell bank. From the seed cell bank, a master cell bank (MCB) was prepared in serum- and protein-free medium, and individual ampoules were frozen off for the further preparation of a working cell bank. Departing from an individual ampoule, a working cell bank was prepared in serum- and protein-free medium. The cells were immobilized on porous microcarriers and continued to be cultured for several generations under serum- and protein-free conditions. At different points of time the cells were assayed for their productivity in serum- and protein-free medium by means of immunofluorescence with labeled anti-vWF antibodies. Evaluation of the stability of the cells was effected at the working cell bank stage and after 10 and 60 generations in serum- and protein-free medium. At the working cell bank stage (FIG. 2A) and also after 10 (FIG. 2B) and 60 generations (FIG. 2C), approximately 100% of the cells were identified as positive stable recombinant clones that express rvWF.

Example 3

Cell-Specific Productivity of the Recombinant Cell Clones

From defined stages during the culturing of recombinant cells, a defined number of cells was taken and incubated with fresh medium for 24 h. The rvWF:Risto-CoF activity was determined in the cell culture supernatants. Table 1 shows that the cell specific productivity in the inventive stable recombinant cell clones was still stable even after 60 generations in serum- and protein-free medium and was even higher in comparison to the original clone that had been cultured in serum-containing medium.

TABLE 1

| Cell Clone | Cell specific productivity of the working cells mU rvWF/$10^6$ cells/day | Cell specific productivity after 10 generations mU rvWF/$10^6$ cells/day | Cell specific productivity after 60 generations mU rvWF/$10^6$ cells/day |
| --- | --- | --- | --- |
| rvWF-CHO #808.68 Original cell clone | 55 | 30 | <10 |
| r-vWF-CHO F7 Stable clone | 62 | 65 | 60 |

Example 4

Composition of a Synthetic Serum- and Protein-Free Medium

| Component | g/l | Preferred amount (according to the knowledge at the time of application) in g/l |
| --- | --- | --- |
| Synthetic minimum medium (DMEM/HAM's 12) | 1-100 | 11.00-12.00 |
| Soybean peptone | 0.5-50 | 2.5 |
| L-Glutamine | 0.5-1 | 0.36 |
| NaHCO$_3$ | 0.1-10 | 2.00 |
| Ascorbic acid | 0.0005-0.05 | 0.0035 |
| Ethanol amine | 0.0005-0.05 | 0.0015 |
| Na-selenite | 1-15 µg/l | 8.6 µg/l |
| optional: Synperonic F 68 | 0.01-10 | 0.25 |

Example 5

Culturing of rFVIII-CHO Cells in Protein- and Serum-Free Minimum Medium

A cell culture containing rFVIII-CHO cells was cultured in a 10 l stirring tank and with perfusion. A medium according to Example 4 was used. The cells were immobilized on a porous microcarrier (Cytopore©, Pharmacia) and cultured for at least 6 weeks. The perfusion rate was 4 volume exchanges/day, the pH was at 6.9-7.2, the O$_2$ concentration was approximately 20-50%, the temperature was 37° C.

Figure 3:
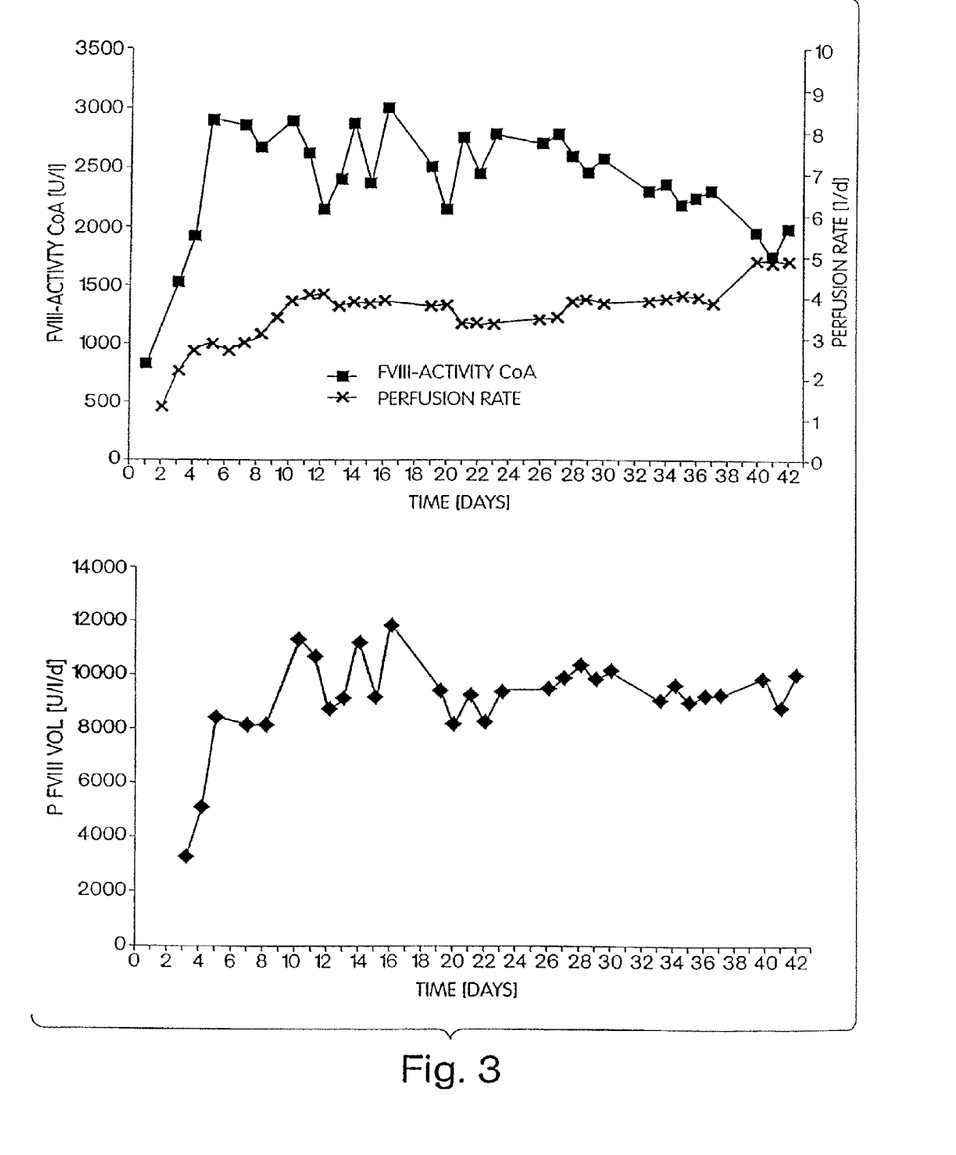
FIG. 3 shows the results of culturing an rFVIII-CHO cell clone in a 10 l perfusion bioreactor.

FIG. 3 shows the results of culturing an rFVIII-CHO cell clone in a 10 l perfusion bioreactor.
  a) F VIII-activity (mUnits/ml) and perfusion rate (1-5/day) over a period of 42 days.
  b) Volumetric productivity (units factor VIII/l/day) in the perfusion bioreactor.

| Days of culturing | Cell-specific productivity mU/$10^6$ cells/day | Immunofluorescence (% FVIII-positive cells) |
| --- | --- | --- |
| 15 | 702 | not indicated |
| 21 | 1125 | not indicated |
| 28 | 951 | >95% |
| 35 | 691 | >95% |
| 42 | 970 | not indicated |

Table 2 shows the stability and specific productivity of the rFVIII-expressing cells. For these results, samples were taken after 15, 21, 28, 35 and 42 days, centrifuged at 300 g and re-suspended in fresh serum- and protein-free medium. After further 24 h, the factor VIII concentration in the cell culture supernatants and the cell number were determined. Based on these data, the specific FVIII productivity was calculated.

A stable average productivity of 888 mUnits/$10^6$ cells/day was attained. This stable productivity was also confirmed by immunofluorescence with labeled anti-FVIII antibodies after 15, 21, 28, 35 and 42 days in serum- and protein-free medium.

Example 6

Comparison of the Productivity of Recombinant FVIII-CHO Cells in Protein- and Serum-Free Medium Containing Additional Medium Components A cell culture containing rFVIII-CHO cells was cultured using a batch method. A medium according to example 4 was used to which the following amino acids were added:

| Amino acid | mg/l | Preferred amount (according to the knowledge at the time of application) in mg/l |
| --- | --- | --- |
| L-asparagine | 1-100 | 20 |
| L-cysteine•HCl•H$_2$0 | 1-100 | 15 |
| L-cystine | 1-100 | 20 |
| L-proline | 1-150 | 35 |
| L-tryptophan | 1-100 | 20 |
| L-glutamine | 50-1000 | 240 |

The cells were cultured at 37° C., pH 6.9-7.2. The cells were cultivated over a period of 24-72 hours in a batch process.

The productivity of the recombinant FVIII-CHO cells was measured in the following media compositions:

Mix 1 consisting of serum- and protein-free medium without soybean peptone and additionally containing a mixture of amino acids as listed in the above table Mix 2 consisting of serum- and protein-free medium containing soybean peptone Mix 3 consisting of serum- and protein-free medium containing soybean peptone and a mixture of amino acids as listed in the above table Mix 4 consisting of serum- and protein-free medium containing, in addition, a mixture of amino acids as listed in the above table and 2.5 g/l of purified, ultrafiltrated soybean peptone. The ultrafiltrated soybean peptone was purified by means of chromatography using a Sephadex© column.

Example 7

Culturing of Recombinant FVIII-CHO Cells in Protein- and Serum-Free Medium Using Chemostat Culture A cell culture containing rFVIII-CHO cells was cultured in a 10 l stirred bioreactor tank. A medium according to example 4 not containing soybean peptone but containing an amino acid mixture according to example 6 was used.

The cells were cultivated at 37° C., pH 6.9-7.2; the oxygen concentration was in the range of 20-50% air saturation. In order to determine the titer of factor VIII and the cell concentration in culture supernatant, samples were taken every 24 hours. The total cell concentration was constant from day 2 to day 14. From day 6, ultrafiltrated soybean peptone was added to the medium. The factor VIII productivity is measured by means of a CHROGENIX COA FVIII:c/4 system. The lack of soybean peptone in the continuous culture lead to a marked decrease in factor VIII productivity after a few days, whereas the addition of the soybean peptone resulted in an almost 10-fold increase in productivity. Because said addition did not increase the cell number, this clearly indicates that ultrafiltrated soybean peptone causes a marked increase in productivity, which, however, is independent of cell growth.

What is claimed is:

1. A method for preparing a recombinant polypeptide in a cell culture, comprising: multiplying an isolated stable mammalian recombinant cell clone that has a selection marker and contains a sequence encoding the recombinant polypeptide in a serum- and protein-free medium comprising a mixture of amino acids containing L-asparagine, L-cysteine, L-cystine, L-proline, L-tryptophan and L-glutamine, wherein the stable cell clone is cultured with neither selective pressure for the selection marker nor selection for a polypeptide factor that replaces serum components, preparing a cell culture containing the stable cell clone in a bioreactor, and harvesting the recombinant polypeptide from the culture supernatant.

2. A method of claim 1, wherein L-asparagine, L-cysteine, L-cystine, or L-tryptophan in the mixture is present from about 1 mg/l to about 100 mg/l.

3. A method of claim 1, wherein L-proline in the mixture is present from about 1 mg/l to about 150 mg/l.

4. A method of claim 1, wherein L-glutamine in the mixture is present from about 50 mg/l to about 1000 mg/l.

5. A method of producing a recombinant product under serum- and protein-free conditions on a large technical scale comprising the steps of:
providing an isolated, stable recombinant original cell clone that contains a selection marker, said original cell clone being stable in serum- and protein-free medium for at least 40 generations and expressing a recombinant product,
multiplying said original stable cell clone in serum- and protein-free medium with neither selective pressure for the selection marker nor selection for a polypeptide factor that replaces serum components so as to obtain a cell culture,
culturing said cell culture containing stable cells in a bioreactor, thereby obtaining said recombinant product, and
harvesting said recombinant product from a supernatant of said cell culture.

6. A method of claim 5, wherein said original cell clone is stable in serum- and protein-free medium for at least 50 generations.

7. A method of claim 5, wherein said serum- and protein-free medium is a synthetic minimum medium and further comprises ultrafiltrated soybean peptone.

8. A method of producing a recombinant polypeptide in a cell culture comprising the steps of:
multiplying an isolated stable starting cell clone containing a selection marker expressing a recombinant polypeptide in serum- and protein-free medium with neither selective pressure for the selection marker nor selection for a polypeptide factor that replaces serum components so as to obtain a cell culture,
culturing said cell culture containing stable cells in a bioreactor so as to obtain a cell culture, and
harvesting said recombinant polypeptide from a supernatant of said cell culture.

9. A method of claim 8, wherein the serum- and protein-free medium comprises minimum medium and ultrafiltrated soybean peptone.

10. The method of claim 1, wherein the recombinant polypeptide is Factor VIII.

11. The method of claim 1, wherein the recombinant polypeptide is Factor IX.

12. The method of claim 1, wherein the recombinant polypeptide is Factor VII.

13. The method of claim 1, wherein the recombinant polypeptide is von Willebrand factor (vWF).

14. The method of claim 5, wherein the recombinant product is Factor VIII.

15. The method of claim 5, wherein the recombinant product is Factor IX.

16. The method of claim 5, wherein the recombinant product is Factor VII.

17. The method of claim 5, wherein the recombinant product is vWF.

18. The method of claim 8, wherein the recombinant polypeptide is Factor VIII.

19. The method of claim 8, wherein the recombinant polypeptide is Factor IX.

20. The method of claim 8, wherein the recombinant polypeptide is Factor VII.

21. The method of claim 8, wherein the recombinant polypeptide is von Willebrand factor (vWF).

* * * * *